United States Patent
Buckle et al.

(10) Patent No.: US 9,906,989 B2
(45) Date of Patent: Feb. 27, 2018

(54) APPARATUS, METHOD AND SYSTEM FOR INTEGRATING MOBILE AND SATELLITE PHONE SERVICE

(71) Applicants: Robert K. Buckle, Hertfordshire (GB); Thomas Hafley, Manassas, VA (US)

(72) Inventors: Robert K. Buckle, Hertfordshire (GB); Thomas Hafley, Manassas, VA (US)

(*) Notice: Subject to any disclaimer, the term of this patent is extended or adjusted under 35 U.S.C. 154(b) by 0 days.

(21) Appl. No.: 14/491,777

(22) Filed: Sep. 19, 2014

(65) Prior Publication Data

US 2015/0011220 A1 Jan. 8, 2015

Related U.S. Application Data

(63) Continuation of application No. PCT/US2013/031746, filed on Mar. 14, 2013.

(60) Provisional application No. 61/612,665, filed on Mar. 19, 2012.

(51) Int. Cl.

| | |
|---|---|
| *H04W 36/00* | (2009.01) |
| *H04W 88/06* | (2009.01) |
| *H04B 7/185* | (2006.01) |
| *H04W 36/14* | (2009.01) |
| *H04W 88/02* | (2009.01) |
| *H04W 36/18* | (2009.01) |
| *H04M 7/12* | (2006.01) |
| *H04W 88/16* | (2009.01) |

(Continued)

(52) U.S. Cl.
CPC ........ *H04W 36/0022* (2013.01); *H04B 7/185* (2013.01); *H04B 7/18563* (2013.01); *H04W 36/14* (2013.01); *H04W 36/18* (2013.01); *H04W 88/02* (2013.01); *H04W 88/06* (2013.01); *H04M 7/12* (2013.01); *H04W 36/30* (2013.01); *H04W 36/36* (2013.01); *H04W 88/16* (2013.01)

(58) Field of Classification Search
CPC ......... H04W 36/0005; H04W 36/0022; H04W 36/0066; H04W 36/18; H04W 36/30; H04W 36/32; H04W 88/02; H04W 88/06; H04B 7/185; H04B 7/18563
USPC .......... 455/436, 439, 442, 444; 370/331–332
See application file for complete search history.

(56) References Cited

U.S. PATENT DOCUMENTS

| | | |
|---|---|---|
| 5,303,286 A | 4/1994 | Wiedeman |
| 5,414,432 A | 5/1995 | Penny, Jr. et al. |
| 5,490,284 A | 2/1996 | Itoh et al. |

(Continued)

FOREIGN PATENT DOCUMENTS

| | | |
|---|---|---|
| FR | 2794596 A1 | 12/2000 |
| JP | 2002500493 A | 1/2002 |

(Continued)

OTHER PUBLICATIONS

PCT/US2013/031746, Buckle et al., Search Report and Written Opinion dated Jun. 7, 2013, ISA/US, 8 pages.

(Continued)

*Primary Examiner* — Magdi Elhag
(74) *Attorney, Agent, or Firm* — Jones Walker LLP

(57) ABSTRACT

A communications system which allows for the integration of mobile and satellite communication networks, which includes an interface device configured to bi-directionally communicate with a mobile device (preferably wirelessly), that includes a satellite antenna on the communications device and a voice/data modem configured to bi-directionally communicate with a satellite network via the antenna.

17 Claims, 9 Drawing Sheets

(51) Int. Cl.
*H04W 36/30* (2009.01)
*H04W 36/36* (2009.01)

(56) References Cited

U.S. PATENT DOCUMENTS

| | | | |
|---|---|---|---|
| 5,504,493 | A | 4/1996 | Hirshfield |
| 5,552,798 | A | 9/1996 | Dietrich et al. |
| 5,581,268 | A | 12/1996 | Hirshfield |
| 5,586,165 | A | 12/1996 | Wiedeman |
| 5,592,481 | A | 1/1997 | Wiedeman et al. |
| 5,619,525 | A | 4/1997 | Wiedeman et al. |
| 5,628,049 | A | 5/1997 | Suemitsu |
| 5,634,190 | A | 5/1997 | Wiedeman |
| 5,640,386 | A | 6/1997 | Wiedeman |
| 5,664,006 | A | 9/1997 | Monte et al. |
| 5,697,050 | A | 12/1997 | Wiedeman |
| 5,732,359 | A | 3/1998 | Baranowsky, II et al. |
| 5,758,260 | A | 5/1998 | Wiedeman |
| 5,758,261 | A | 5/1998 | Wiedeman |
| 5,778,322 | A * | 7/1998 | Rydbeck ............ H04B 1/3816 455/454 |
| 5,791,598 | A | 8/1998 | Rodden et al. |
| 5,796,760 | A | 8/1998 | Wiedeman et al. |
| 5,802,445 | A | 9/1998 | Wiedeman et al. |
| 5,812,538 | A | 9/1998 | Wiedeman et al. |
| 5,812,932 | A | 9/1998 | Wiedeman et al. |
| 5,859,874 | A | 1/1999 | Wiedeman et al. |
| 5,867,109 | A | 2/1999 | Wiedeman |
| 5,875,180 | A | 2/1999 | Wiedeman et al. |
| 5,884,142 | A | 3/1999 | Wiedeman et al. |
| 5,896,558 | A | 4/1999 | Wiedeman |
| 5,905,943 | A | 5/1999 | Wiedeman et al. |
| 5,912,641 | A | 6/1999 | Dietrich |
| 5,914,675 | A | 6/1999 | Tognazzini |
| 5,918,157 | A | 6/1999 | Wiedeman et al. |
| 5,956,619 | A | 9/1999 | Gallagher et al. |
| 6,072,768 | A | 6/2000 | Wiedeman et al. |
| 6,134,437 | A | 10/2000 | Karabinis et al. |
| 6,278,876 | B1 * | 8/2001 | Joshi ............ H04B 7/18517 455/427 |
| 6,529,707 | B1 | 3/2003 | Dent |
| 6,614,769 | B1 | 9/2003 | Erlick et al. |
| 6,661,966 | B1 | 12/2003 | Weideman et al. |
| 6,711,417 | B1 * | 3/2004 | Gorman ............ H04W 92/06 370/395.52 |
| 7,274,908 | B1 | 9/2007 | Boone et al. |
| 7,463,882 | B2 | 12/2008 | Tuomela et al. |
| 7,667,643 | B2 | 2/2010 | Handermann et al. |
| 7,693,101 | B2 | 4/2010 | Gernert et al. |
| 7,826,868 | B2 * | 11/2010 | Robbins ............ H04M 3/42314 455/426.1 |
| 8,223,717 | B2 * | 7/2012 | Dillon ............ H04L 29/12188 370/331 |
| 8,676,121 | B1 | 3/2014 | Monte et al. |
| 2003/0104809 | A1 * | 6/2003 | Godshaw ............ H04M 1/725 455/426.1 |
| 2004/0266426 | A1 * | 12/2004 | Marsh ............ H04W 36/0066 455/426.2 |
| 2005/0090259 | A1 * | 4/2005 | Jain ............ H04L 29/06 455/439 |
| 2006/0025141 | A1 * | 2/2006 | Marsh ............ H04W 36/0066 455/445 |
| 2006/0171359 | A1 | 8/2006 | Schwarz |
| 2006/0259416 | A1 | 11/2006 | Johnson |
| 2007/0123252 | A1 * | 5/2007 | Tronc ............ H04B 7/18563 455/427 |
| 2007/0183440 | A1 | 8/2007 | Bennet et al. |
| 2007/0186251 | A1 | 8/2007 | Horowitz et al. |
| 2007/0206522 | A1 | 9/2007 | Starke et al. |
| 2008/0025249 | A1 | 1/2008 | Kuppuswamy et al. |
| 2009/0047016 | A1 | 2/2009 | Bernard et al. |
| 2009/0168974 | A1 | 7/2009 | McCormick |
| 2009/0180421 | A1 | 7/2009 | Hall et al. |
| 2009/0260004 | A1 | 10/2009 | Datta et al. |
| 2010/0029273 | A1 | 2/2010 | Bennett |
| 2010/0150110 | A1 | 6/2010 | Dutta et al. |
| 2010/0159922 | A1 | 6/2010 | Tronc et al. |
| 2010/0265957 | A1 | 10/2010 | Foxworthy et al. |
| 2011/0046842 | A1 | 2/2011 | Smith |
| 2012/0051405 | A1 | 3/2012 | Piesinger |
| 2012/0149364 | A1 | 6/2012 | Leedom, Jr. |
| 2013/0053095 | A1 | 2/2013 | Buckle |
| 2013/0189975 | A1 | 7/2013 | Wyler |
| 2014/0071886 | A1 | 3/2014 | Monte et al. |

FOREIGN PATENT DOCUMENTS

| | | |
|---|---|---|
| JP | 2004096265 A | 3/2004 |
| JP | 2007235492 A | 9/2007 |
| WO | 9628947 A1 | 9/1996 |
| WO | 2006094564 A1 | 9/2006 |
| WO | 2013142284 A1 | 9/2013 |

OTHER PUBLICATIONS

Lampropoulos, George, et al. "Handover management architectures in integrated WLAN/cellular networks." IEEE Communications Surveys and Tutorials 7.1-4 (2005): 30-44.

Hong, Tae Chul, et al. "Inter-system handover analysis in integrated terrestrial and GEO satellite communication networks for seamless mobility." Advanced Communication Technology, The 9th International Conference on. vol. 1., pp. 717-721. IEEE, 2007.

Corazza, G. E., et al. "Handover procedures in integrated satellite and terrestrial mobile systems." Proceedings of the Third International Mobile Satellite Conference IMSC (1993), p. 143-148.

Baranowsky II, Patrick W. "MSAT and cellular hybrid networking." Proceedings of the Third International Mobile Satellite Conference IMSC (1993), p. 149-154.

Lott, M., et al. "Interworking of WLAN and 3G systems." Communications, IEE Proceedings-. vol. 151. No. 5. IET, 2004.

"Globalstar Launches Satellite Data and Voice Module in the United States." May 29, 2007, Thomasnet News, retrieved on Jul. 3, 2014 from http://news.thomasnet.com/companystory/Globalstar-Launches-Satellite-Data-and-Voice-Module-in-the-United-States-521501.

"Freescale Unveils Embedded VoIP Reference Platform Solution." Oct. 8, 2007, EE Times India, retrieved on Jul. 3, 2014 from http://www.eetindia.co.in/ART_88000482580_1800001_NP_d8a9f35a.HTM.

"iChip Co2144." Feb. 25, 2010, Connect One, retrieved on Jul. 3, 2014 from http://web.archive.org/web/20100225021143/http://www.connectone.com/products.asp?did=40&pid=75.

PCT Application No. US2012/024177; International Search Report for Applicant Globalstar, Inc. dated Jun. 1, 2012.

* cited by examiner

Vertical Handover SoftSwitch Components

The VHSG is a combination of four separate sub-systems, they are: Mobile Operator Interface (MOI), Users Channel Module (UCM), SoftSwitch (SS) and the Media Changer (MC)

MOI

The MOI is to allow the UCM to connect directly to the MNO via one of three ways; UMA (GANC), Femtocell or Air-Interface. This enables the VHSG to have a direct connection with the MNO using standard user agreements and without needing any special roaming contracts.

UCM

The UCM consists of multiple channel modules which hold the user's Subscriber Identity Module (SIM) cards. Each subscriber is allocated a SIM card which holds their ported UCM.

SS

The SoftSwitch is a multi process which runs all the core functions.

MC

The media changer is a combination of hardware and software which allow the SS to interface with different media such as PSTN, ISDN, and IP.

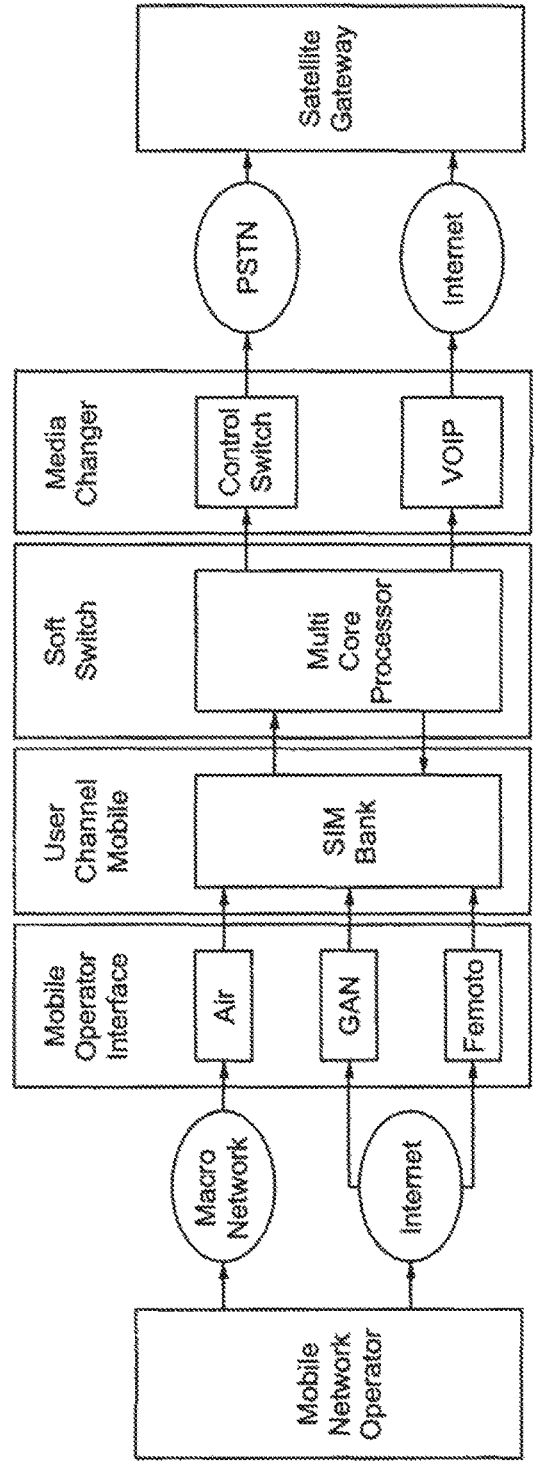

Figure 4

- 1720 Voice / Data Modem
- Media Changer
- Autonomous Radio Core
- Air Interfaces:
  2G / 3G / Wifi / Bluetooth
- Voip Sip Server
- Dynamic Web Cash (Optional)
- Email Server (Optional)

APPARATUS, METHOD AND SYSTEM FOR INTEGRATING MOBILE AND SATELLITE PHONE SERVICE

PRIORITY CLAIM

This application is a continuation of PCT/US2013/031746 filed on Mar. 14, 2013, which claims the priority benefit of U.S. provisional application No. 61/612,665 filed on Mar. 19, 2012, the contents of which are hereby incorporated by reference.

FIELD OF THE INVENTION

The present disclosure relates generally to mobile phones, and more particularly to an apparatus, method, and system for integrating mobile and satellite telephone service.

BACKGROUND

Various types of wireless communication systems are in global use, including a satellite phone network and a mobile or cellular phone network. Although satellite phones are well known, these types of devices possess a number of limitations regarding range of use, telephone number portability to non-satellite networks, extended development time, cost and the like. The range of use of existing satellite phones is likewise limited as these devices will not transmit or receive phone calls if the operator is located indoors. Accordingly, an operator of a satellite phone must be located outdoors in order to access the satellite and to utilize the device for its intended purpose.

Existing satellite phones are further limited regarding telephone number portability to non-satellite networks. More specifically, telephone numbers assigned to a satellite handset device cannot be ported for use on non-satellite networks (e.g., public mobile networks). Conversely, mobile phones presently enjoy telephone number portability between different mobile networks.

Similar to satellite phones, mobile devices likewise posses a number of limitations that constrict their usage. For example, the user must be in the vicinity of a cellular tower associated with the network in order to receive and place calls. Dropped phone calls may occur while switching between cellular towers. If the user is located in a remote location outside the range of a cellular tower, then the mobile device will not function as a communications device.

A consumer in need of broad phone coverage would have to use both a cellular phone and a satellite phone, each having a separate phone number. Thus, there is a need in the art for a system to allow a mobile phone to emulate a satellite phone and in addition, to have an option to transfer an ongoing call from the satellite system to the mobile system (and back) without the user's intervention and without interrupting the ongoing call.

SUMMARY OF THE DISCLOSURE

A communications system provided herein which allows for the integration of mobile and satellite communication networks. The communication system device includes an interface device configured to bi-directionally communicate with a mobile device (preferably wirelessly), that includes a satellite antenna on the communications device and a voice/data modem configured to bi-directionally communicate with a satellite network via the antenna. The communications system may or may not also include a softswitch device that interfaces both satellite systems and accesses mobile networks via either the internet or via the mobile network.

DESCRIPTION OF THE DRAWINGS

FIG. 4 is a block diagram of depicting some of the components of one embodiment of a VHSG.

DESCRIPTION OF THE PREFERRED EMBODIMENT

Figure 1:
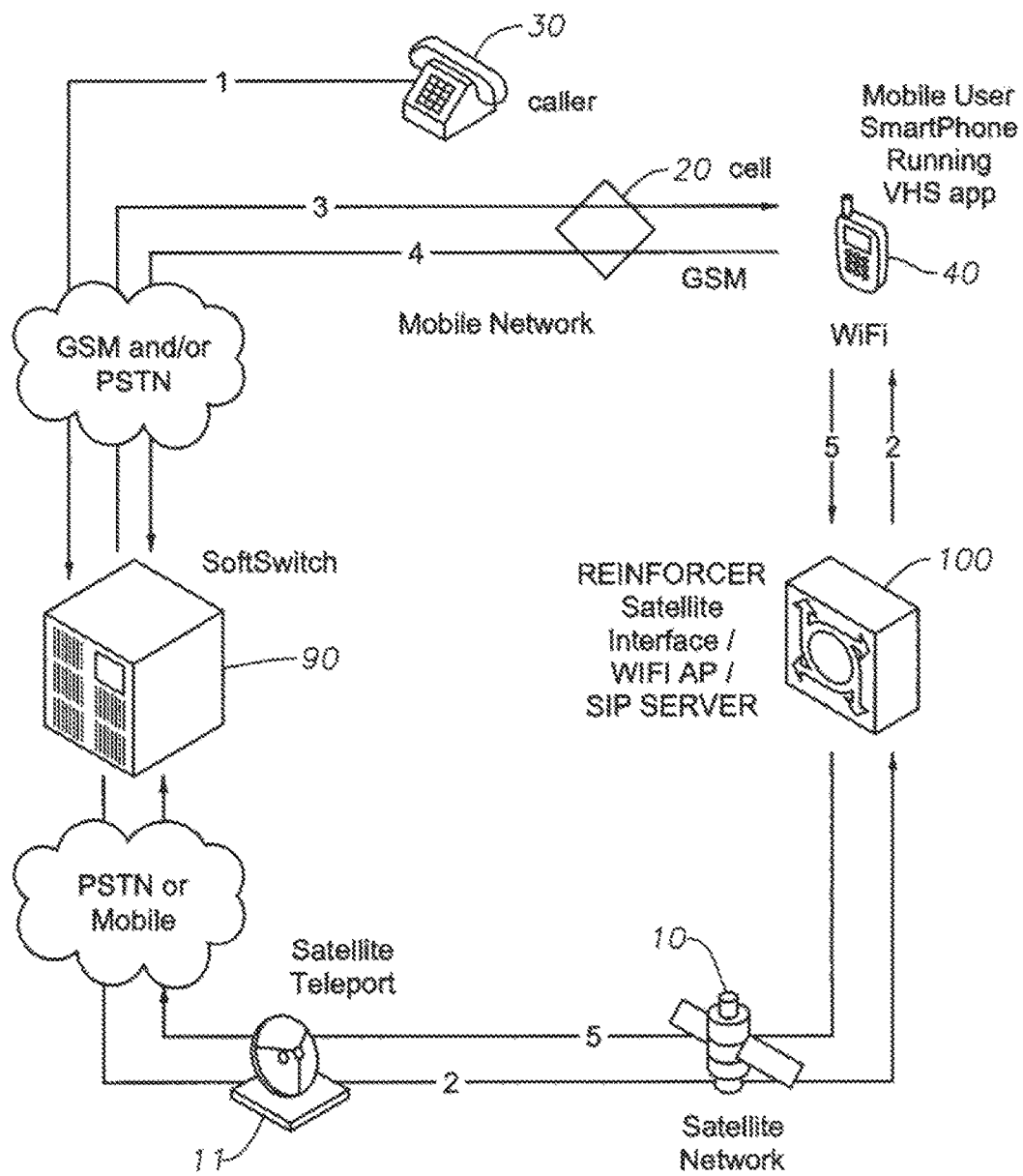
FIG. 1 depicts the system used to transfer calls between networks.

Traditional cellular or mobile networks include mobile devices (cell enabled devices) such as smart phones, that communicate wirelessly to cellular towers 20, which then route received calls to another communications device, such through a gateway to the public switched telephone network, or another mobile network. As used herein, a mobile communications network is a radio enabled cellular network where the mobile device 40 directly communicates though a cell 20 which interfaces with the public switched telephone network, another cell network, or the internet). A satellite communications network includes satellite communications devices, such as a satellite phone, that communicates directly to a satellite 10, which then redirects the call to a satellite gateway 11 for routing the satellite call via the public switched telephone network to another communications device. A systems diagram of an integrated wireless phone communications network is illustrated in FIG. 1. The integrated wireless phone communications network bridges the gap between cellular phone coverage via a network of cellular towers and satellite phone coverage via a network of satellites. The communications network further includes a conventional satellite network (depicted by the satellite 10 and satellite gateway 11) which communicates through satellite gateways 11 to a core network (including packet data routing systems) which ultimately transfers information to the Internet or a public switched telephone network (or PSTN). As background information, for both mobile and satellite communication devices, information is transmitted across the respective communications network digitally. In conventional satellite and mobile cell phones, the processor in the phone converts the analog voice signal for transmission to a digital outgoing signal, and vice versa for incoming digital voice data.

The present system includes a softswitch 90 or vertical handover softswitch gateway (VHSG) (sometimes referred to as a switch device) that interfaces between a mobile network and a satellite network (and may access these networks though PSTN, a mobile network, the internet or intranet, or some other connection) as later described. The system includes the use of a mobile device, such as a mobile "smart" phone. Various examples of a smart phone include iPhone®, Blackberry®, Android® or the like. The mobile device may be a laptop, tablet or other device that can communicate wirelessly over a mobile network. Many of these devices, e.g., smart-phones, are capable of converting an analog voice signal into a VoIP data stream and sometimes will be referred to as "VoIP transmitting devices." In the description that follows, the mobile device is referenced as a mobile phone for convenience, but the invention is not so limited. The mobile phone is capable of wireless communications via a public mobile network. The public mobile network includes a plurality of cellular towers 20 geographically positioned in order to provide cellular phone coverage within range of the cellular tower. A mobile number is associated with the mobile phone for identification purposes, as is conventionally deployed in a Subscriber Identity Module (SIM) card (for GSM networks) or Re-Useable Identification Module (RUIM) cards (for CDMA networks) (both referred to herein as "SIM" cards) or some other type of SIM-like device (all referred to herein as a "SIM card"). The system also uses an adapter 100 for each associated mobile device, also referred to as a signal reinforcer or reinforcer, in operative communications with the mobile phone (or other mobile device) in a manner to be later described.

The communications system may include a softswitch 90 and related equipment that communicates with the public telephone switched network (PTSN) and mobile networks, and via either networks, to a satellite network. The softswitch 90 enables an ongoing "call" to or from a mobile device to be switched from the satellite network to mobile network (and vice versa) without "dropping" the call. Advantageously, the softswitch 90 can operate over any public communications network without special agreements or arrangements. As such, the selection of which network operator to use to interconnect with for outbound calls is very flexible.

Softswitch or Vertical Handover SoftSwitch Gateway (VHSG).

The purpose of the VHSG or Softswitch 90 is to enable in-progress calls to be seamlessly transferred from one communications network to another without dropping the call. In telecommunication terms this process is known as soft "Hand-Over" or "Hand-Off." The handover pertinent to this invention is from a mobile network to a satellite network, or vice versa. The conventional way for Public Mobile Operators (PMO) to interconnect together is via an SS7 inter-MSC link, however this link protocol does not support handover of live calls from one network to another. Aspects of the Softswitch are shown in block diagram in FIG. 4.

The ability of the Softswitch 90 to achieve handover lies in its ability to continually "anchor" or monitor all in-progress inbound and outbound calls to or from the mobile device through the Softswitch's processor or central controller. One of the benefits of the VHSG system is that while the subscriber is connected to the PMO's network, all calls are routed directly to the subscriber via the Softswitch 90 and not "tromboned" through a switch, that is, the call is multiplexed within the public mobile operator's network. This ensures the quality and latency of the call remains the same as normal. Note that the "anchoring" described is not the same as routing all calls through the Softswitch.

Set Up.

In order for the VHSG to control calls, a user or subscriber must first have a mobile device that is serviced by a PMO. Each subscriber is then able to register with the System that includes the VHSG. Once registered and set up, as described, calls to or from the mobile device will be directed (if the call is placed via the PMO network) or routed (if the call is placed via the satellite network) by the VHSG. To set up the subscriber with the VHSG, at least two SIM cards are used. One SIM card is located at the mobile device 40, another located at or in communication with the processor of the VHSG. 90 The subscriber user may have an additional optional identifier, used to enable the subscriber's mobile device to access the VHSG, preferably via a satellite network, and this is designated as their User Access Number (UAN), and can be, for instance, an IP address, a land phone number, or an third SIM card. The UAN appears to the PMO and PSTN as a valid destination or identifier for routing calls.

The subscriber's mobile device 40 has a PMO associated with the device, and a subscriber identifier (such as a cell telephone number) associated with that device (stored on a SIM card or other similar device). A second identifier (such as a second cellular phone number) will be associated with the subscriber, preferably associated with the subscriber's PMO (but not necessarily), and stored on a device such as a SIM card. The SIM card located on the mobile 40 device will be denoted the "secondary SIM," while the SIM card located or associated with the VHSG 90 will be denoted the "primary SIM" (generally, the primary SIM will be associated with the user's original mobile phone number). The primary SIM subscriber identifier (e.g. mobile phone number) is designated as their User Gateway Number (UGN), while the secondary SIM has a second subscriber identifier and is designated the User Mobile Number (UMN). The primary and secondary SIM identifiers can be from any PMO, and will be "paired" together or associated in the system (e.g. system database). In practice, it is preferred that (1) the two SIM cards are related to each other in a database for call management purposes and (2) they are paired via a friends and family type payment plan so that there is a cost effective plan to cover the fact that two SIM cards will be active on the PMOs network instead of one.

In the discussion which follows, the secondary SIM will be located with the user's mobile phone 40, while the primary SIM will be stored and in communications with the Softswitch's 90 central processor. The primary SIMs of all subscribers to the service will be described as stored in a "SIM Bank," a facility that plugs each subscriber's primary SIM into a storage device that enables the banked SIM card to communicate with each subscriber's PMO (such as through a pico cell, a micro cell, femto cell, gnac or other such device. (e.g. the secondary SIM looks to the PMO as an "active mobile device" to which it can communicate via a cell tower)). The Softswitch central processor also is able to communicate with each SIM card, and the processor monitors communications and handshaking at and through the banked SIM cards. The SIM bank will generally be collocated with the softswitch, but this in not required. If UAN's are utilized, the VHSG can employ the UAN through an IP gateway (for IP addresses), or an exchange, such as a private branch exchange (PBX), for land line numbers.

Another additional identifier is also allocated or associated to the subscriber, the satellite identifier (e.g. a satellite phone number) and is designated as their User Satellite Number (USN).

Operation.

Once the subscriber is set up and registered with the communications system, the database associated with the Softswitch's processor will cross reference or associate all of a subscribers identifiers (primary and secondary SIM, satellite, USN and if applicable, UAN). Additionally, the VHSG may have modems or other hardware/software to assist in proper communications to the PSTN, the mobile network or the internet, as needed, such as A/D converters, modems, codecs, reformatting algorithms, session initiation protocol servers (SIP) for Voiceover IP (VoIP) communications, etc. This communications equipment is generally referred to as a "Media Changer." In the discussion that follows, several different numbers and SIM cards are being used within the system, but these are completely transparent to the subscriber and a party calling that subscriber. The subscriber continues to make and receive calls using the subscriber identifier (the identifier associated with the primary SIM), as next described.

Figure 3A:
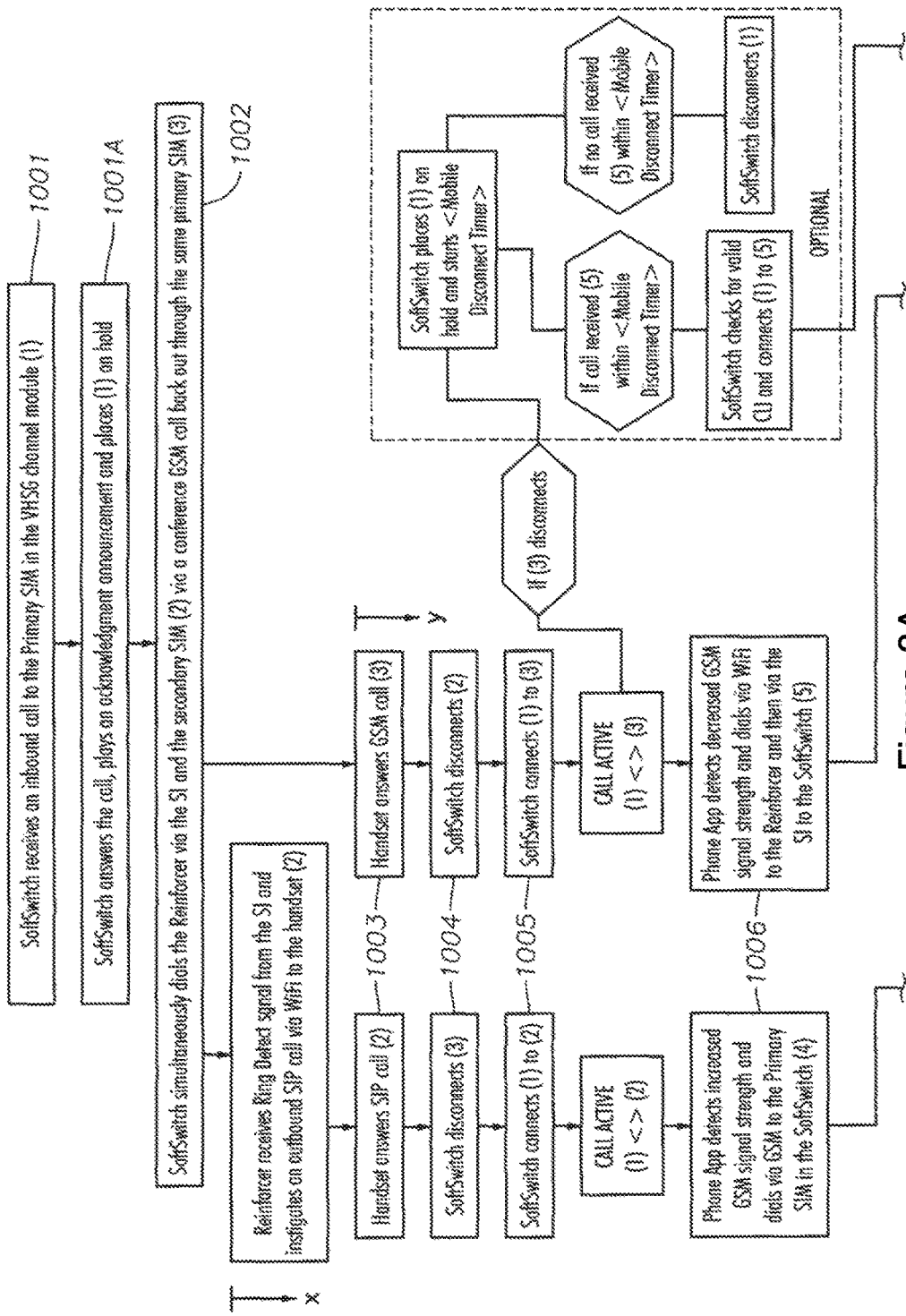
FIGS. 3A and 3B depicts the flow of an inbound call to the mobile device in one embodiment of the system.
Figure 3B:
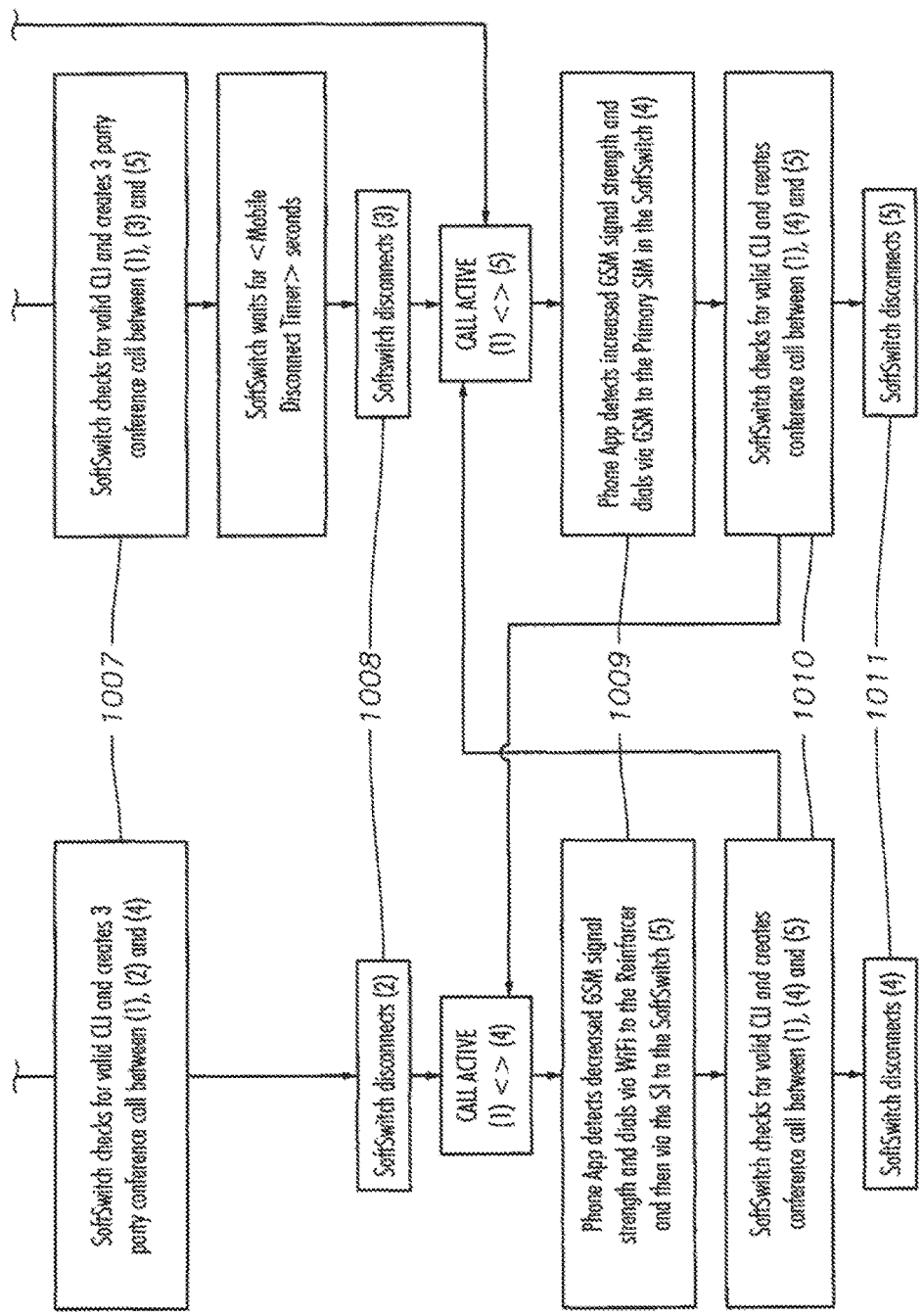

Inbound Calls (FIG. 1 and FIGS. 3A and 3B).

In FIGS. 2A and 2B and 3A and 3B, a reference to a number in parenthesis, (such as (1), (3), (5)), reference a communications path shown in FIG. 1. For instance (2) is a communications path between the mobile device 40 and the Softswitch 90 (via the reinforcer 100 and satellite network SI (10,11)). When a call is the made to the subscriber's primary subscriber identifier, that call is routed, through the mobile network, to the primary SIM located at or in communication with the VHSG. The VHSG, monitoring calls at the primary SIM, is aware that a call is directed to the primary SIM, and will recognize this as a call from a third party to the primary SIM from the caller ID (that is, the caller ID does not indicate the calling party is identified with the secondary SIM or the USN) (step 1001). The Softswitch, detecting an inbound call, "answers" the call and then initiates two outbound calls (step 1002), each associated with the primary SIM—the first call is a conference call through the mobile network to the secondary SIM (i.e. to the UGN) leg Y (depicted as path 3 in FIG. 1), and the second call to the UGN, leg X (depicted as path 2 in FIG. 1), which preferably, is a call placed via the UAN. Alternatively, both calls may be a separate conference call, or each can be made as a leg of a single conference call through the primary SIM. The call to the USN (leg X) will be routed, over the PSTN to the satellite gateway 11 and thence over the satellite network, to the reinforcer 100 (later described) that is in communication with the mobile device 40. The reinforcer 40 allows the mobile device to operate or emulate as a satellite phone and manages satellite communications with the mobile device in conjunction with an applications program (an "app") on the mobile device. The reinforcer will notify the application program resident on the mobile device of an incoming satellite call from the softswitch (and may be identified by caller ID, (for instance, as identified as the UAN)). If the delays in establishing the calls are excessive, the Softswitch may optionally transmit a message to the third party (e.g. "attempting to reach xxx-xxxx, or simply provide ring tone back to the third party) or place the third party on hold (step 1001A).

Generally, because the satellite network is slower in establishing a communications link, the first call to "reach" the subscriber's mobile device 40 will generally be the call directed over the mobile network to the UGN (unless the subscriber is not in good signal range of a cell tower). In any event, the subscriber answers one of the incoming calls. Because the call to the mobile device is "placed" by the VHSG via the primary SIM (or the UAN), the VHSG remains in the communications loop on the calls to the mobile device. While in the communications loop, the VHSG receives and/or provides handshaking information, such as that needed to establish and tear down a call. Hence, the VHSG is able to detect which outgoing call has been answered (the mobile call to the secondary SIM or the satellite call to the USN).

Once the subscriber "picks up" or answers one of the incoming calls at the mobile device, (step 1003X or 1003Y), the VHSG will either direct the call that was answered at the mobile device (1003X or 1003Y) to the third party caller, (if the call is answered via the secondary SIM card) (step 1005Y) or routes the answered call to the third party call (if the satellite call is answered) (step 1005X). The VHSG also drops or disconnects the non-answered call or the leg of the conference call that is not answered (step 1004X or 1004Y). However, as the softswitch 90 placed the call answered by the mobile device, the softswitch 90 remains a "participant" on the resulting call between the mobile device 40 and the third party 30, monitoring the call for handshaking or other pertinent call progress information.

Using conference calls via the primary SIM card also implies that the third party call is not being tromboned through the VHSG, instead, it is being multiplexed at the PMO.

Handing Over an Established On-Going Call Between Networks (FIGS. 1, 2A and 2B and 3A and 3B).

The mobile device 40 (and/or the reinforcer) will have an application software package (an "app") that monitors cellular signal strength of the mobile network or otherwise tracks expected signal strength. Based on the signal strength or expected signal strength, it may be desired to switch an ongoing call from one network to another. For instance, if a mobile call is in progress but cellular signal strength is failing, it may be desired to hand over the call to the satellite network. Conversely, if the ongoing call is over the satellite network, and mobile signal strength reaches a sufficient signal strength for a sufficient period of time, it may be desired to hand over the call to the mobile network. It is assumed that the subscriber will prefer to use the mobile network in lieu of the satellite network, primarily from a cost standpoint, but this can be an option that is user set.

"Hand over" between networks is established as follows, where the "active" network refers to the current network supporting the ongoing call, and the "passive" network refers to the network not currently supporting the ongoing call. In FIGS. 3A and 3B, the call would be transferred from leg Y to leg X, or vice versa.

The resident mobile application (app) determines that a change in signal strength has occurred and a hand over, from the active to the passive network, is desired (step 1006). Instead of, or as an backup to actively monitoring mobile signal strength, the mobile device may have stored thereon information correlating expected poor signal strength with geographic location (or vice versa—good signal strength versus geographic location). For instance, the app may be able to access a "map" of expected poor signal strength, and based upon the current location (or expected location based on trend info), determine that a transfer of networks is desirable. In any event, the app will trigger a call back the VHSG over the passive network (either via (4) or (5)), to the primary subscriber identifier (the primary SIM) (in one embodiment) or to the UAN (if UAN's are utilized). If the passive network is the mobile network (e.g. transfer is from leg X to leg Y), the call is placed via the secondary SIM to the VHSG as a mobile call (route (4); if the passive network is the satellite network (e.g. transfer is from leg Y to leg X), the call is place from the reinforcer to, for instance, the UAN (route(5)). The VHSG 90 will detect an incoming call to the primary SIM or the UAN, and will recognize that the incoming call is from the mobile device 40 or the reinforcer 100 (such as for instance, by using caller identification technology, referenced as "CLI" in the Figures). The VHSG 90, aware that a call to the user is already in progress via the primary SIM, will recognize this second call as a request to hand over or transfer the existing call between networks. The VHSG will then direct or bridge the incoming call from the secondary SIM or reinforcer, into the established ongoing call on the active network (step 1007). At this point, both networks are being utilized to support the call, and hence, both networks are "active." At a predetermined point, the VHSG will then disconnect or drop the leg of the conference call through the original "active" network, which now becomes the "passive" network (step 1008).

Alternatively, the app may send signals over the active network ongoing call (such as using data over voice) to be detected at the VHSG as a "request to hand over," in which event the VHSG may place a call back to the mobile device over the passive network, and let the resident app at the mobile device join both communications channels, and then disconnect the channel to the prior "active" network (not shown in the figures).

Before the VHSG undertakes to drop one of the calls, the reinforcer 100 and mobile app coordinate to hand over the call at the mobile device 40, between the mobile network (leg Y) and satellite network (leg X). For instance, suppose the primary network is the mobile network (leg Y, path (3)), and the satellite network (leg X) is passive. The resident app detects signal strength as failing (outside of set limits) or falling precipitously (trend of signal strength is downward quickly) (step 1009). The resident app on the mobile device 40 then communicates with the reinforcer 100 to establish an outgoing call over the satellite network (leg X path (5), for instance, an outgoing call to the UAN at the VHSG 90 (step 1009). When this outgoing call is "answered" (recognized via CLI) at the VHSG and routed to the currently established call (step 1010), the reinforcer 100 is notified by handshaking signals (such as a tone signal sent by the softswitch) or timing, that is used to reflect the status of the call. The reinforcer 100 notifies the application program resident on the mobile device 40 of the established satellite call, so that app may redirect the ongoing mobile call to the reinforcer 40, for satellite communications (the app may or may not directly move the call, but may wait to redirect based on further indications of signal strength). The redirection of the call at the mobile 40 from the mobile network (leg Y) to the satellite network (leg X), or the disconnection of the call over the mobile network, can be used by the softswitch 90 as an indicator that the mobile device has switched networks, and allow the VHSG to drop or disconnect the now non-used network call (e.g. the now passive network call) (step 1011).

In the example, at this point, the mobile device 40 is now in communication with the third party 30 over the previously passive network (i.e. leg X via the reinforcer and satellite network, to, for instance, the UAN). The call has successfully been handed over to the prior "passive" network (the satellite network) which is now the active network, while the prior active network (the mobile network), is now passive. This handoff is transparent to the subscriber.

Also shown in an optional procedure (which can be used on both the satellite leg or mobile leg) shown on the mobile leg. In this procedure, if the third party disconnects (e.g. the call is dropped, such as due to lack of cell signal to support the call, and not due to the third party hanging up, which would have handshaking associated with a call takedown), the softswitch can wait a predetermined time for the call to be reestablished, and if reestablished, transfer the calls from the passive network to the active network, or if time expires, to tear down the remaining paths of the call.

Figure 6A:
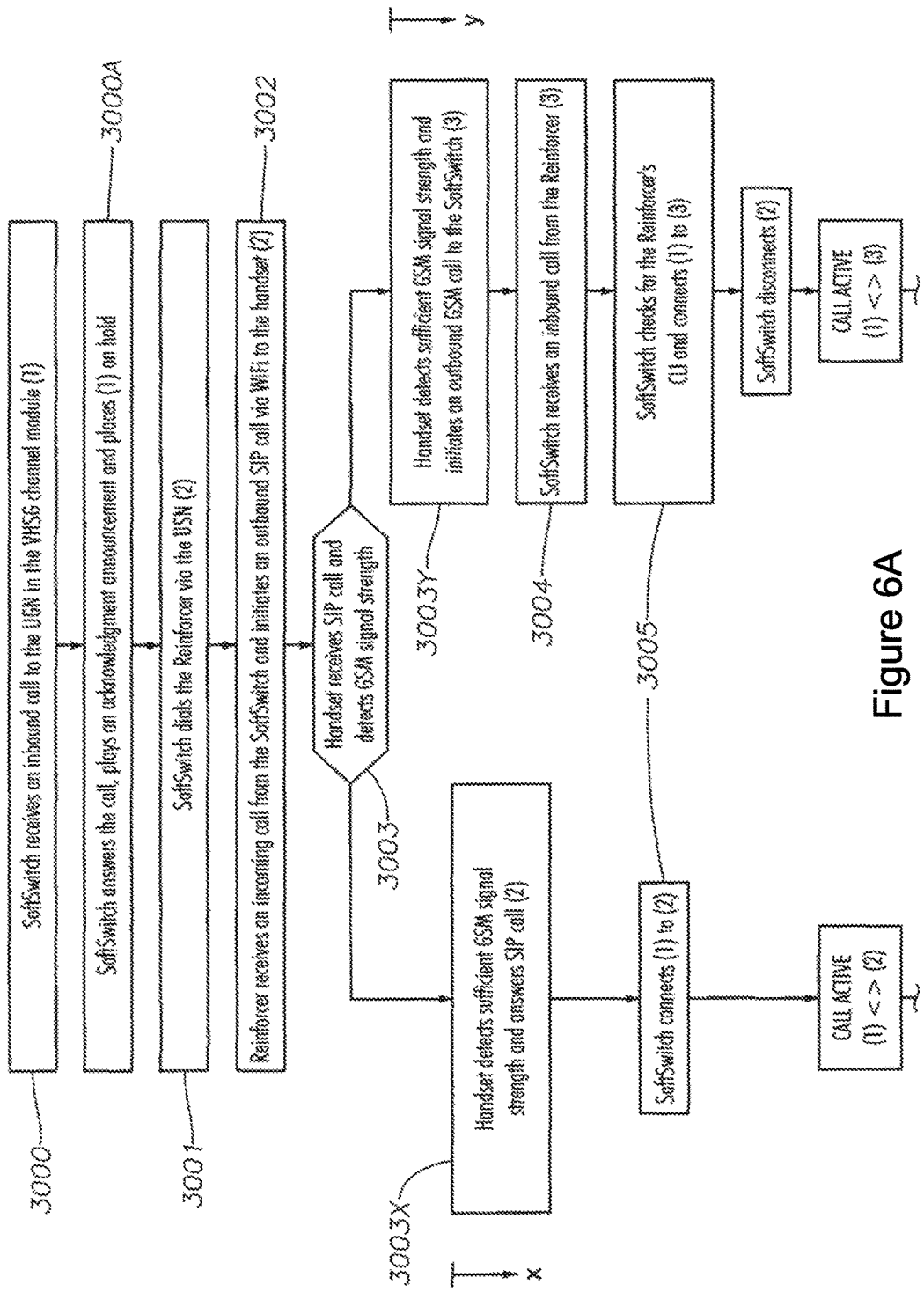
FIGS. 6A and 6B depicts the flow for an inbound call in an alternative embodiment.
Figure 6B:
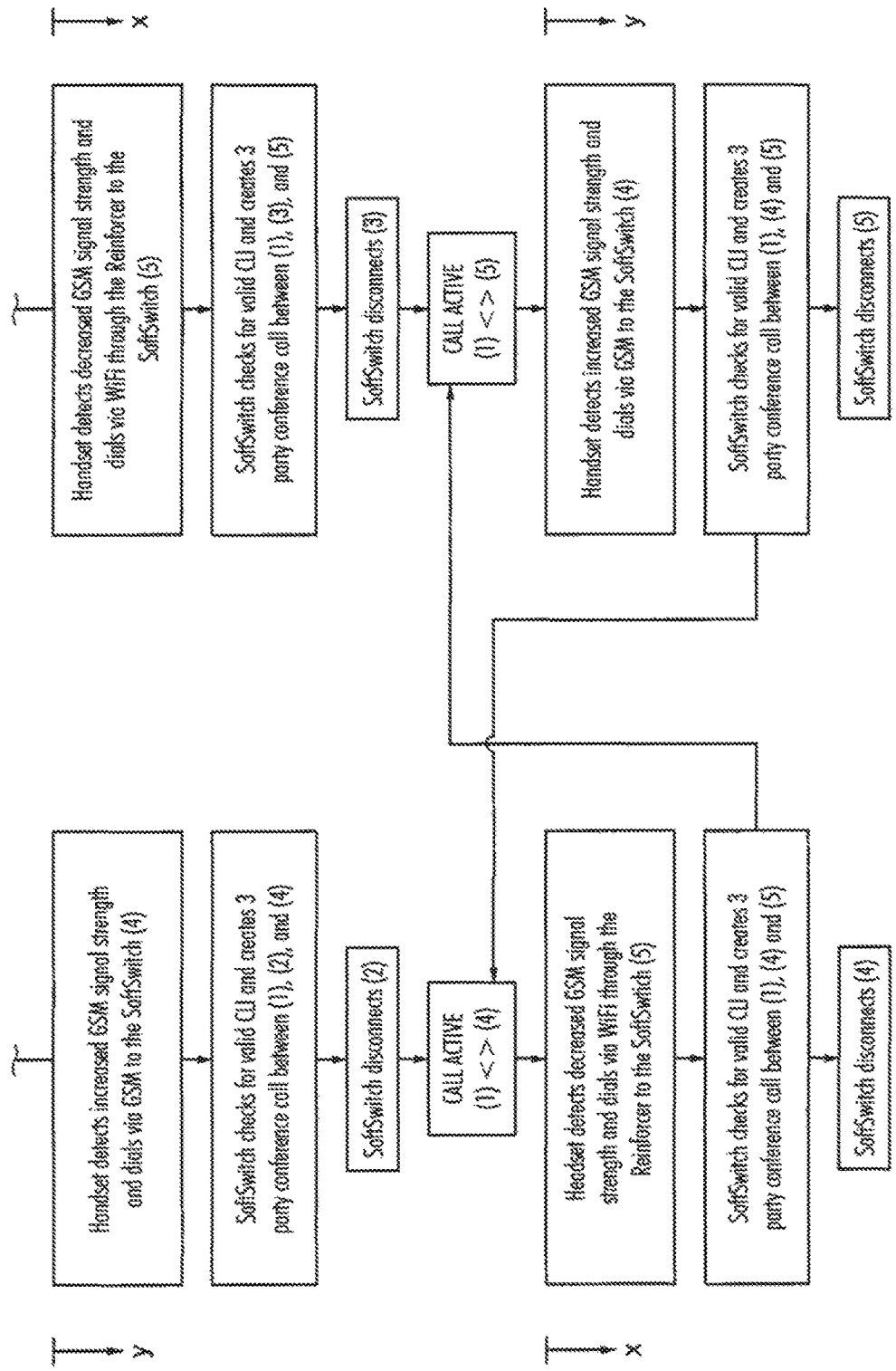

Alternative Inbound Call Handling (FIGS. 1 and 6A and 6B).

Figure 5:
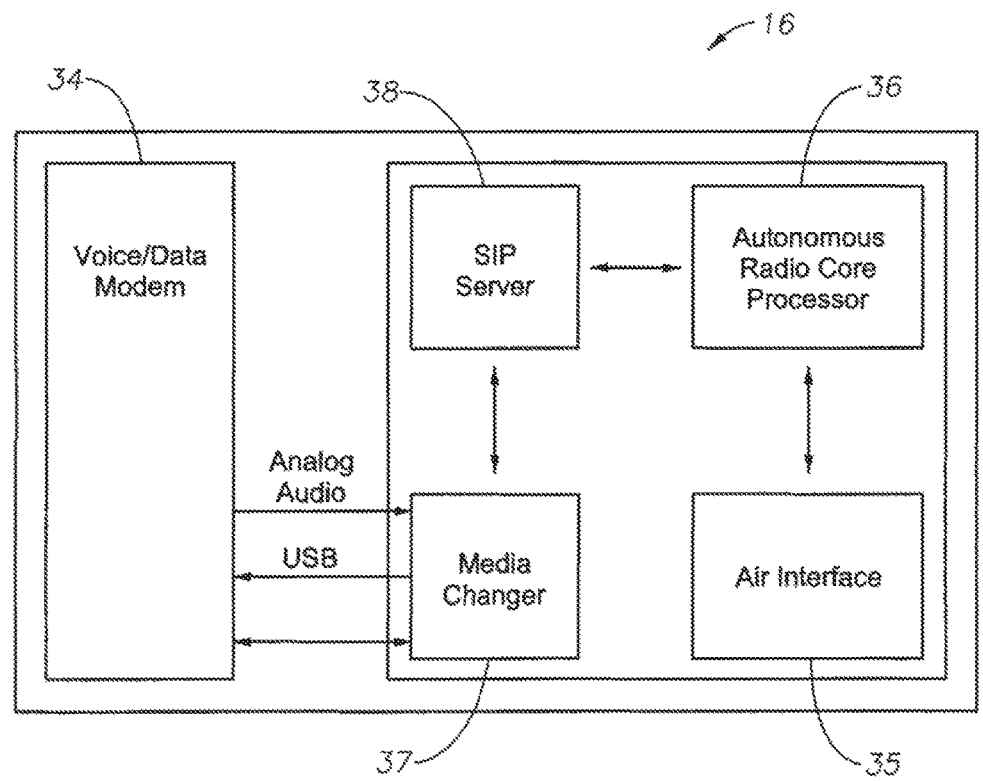
FIG. 5 is a block diagram depicting some of the components of one embodiment of a reinforcer.

In an alternative embodiment depicted in FIGS. 6A and 6B, an inbound call from a third party to the UGN is received at the Softswitch. (step 3000). The softswitch initiates a satellite call to the mobile device (that is, the reinforcer) (step 3001). The reinforcer 100 initiates a session with the mobile app (step 3002—shown as a SIP call via WIFI, as a non-limiting example). The mobile app on the mobile device recognizes that this is notice of a pending incoming call. The mobile app will test the cell signal strength, and based on this signal strength determine the communications network to initially employ for the call (step 3003). If signal strength is low (step 3003X), the mobile app allows the incoming call to be routed through to the mobile device (described as a handset in FIG. 5) (step 3005X). For instance, the mobile app may have the mobile provide notice to the user of an incoming call (e.g. ring the phone), and if the user answers, connect the call to the mobile via the reinforcer and mobile app.

If cell signal strength is high (step 3003Y), the mobile app can initiate a mobile communications call to the softswitch (step 3003Y). The softswitch detects the incoming call as coming from the mobile device (steps 3004 and 3005), and recognizes this call as a request to route the pending incoming call to the mobile network. The softswitch then bridges the incoming mobile call with the incoming third party call (step 3005Y) and drops the satellite leg of the incoming call. The remaining steps in FIGS. 6A and 6B are directed to transferring on ongoing call between networks (e.g. satellite—mobile) as s described above.

Figure 2A:
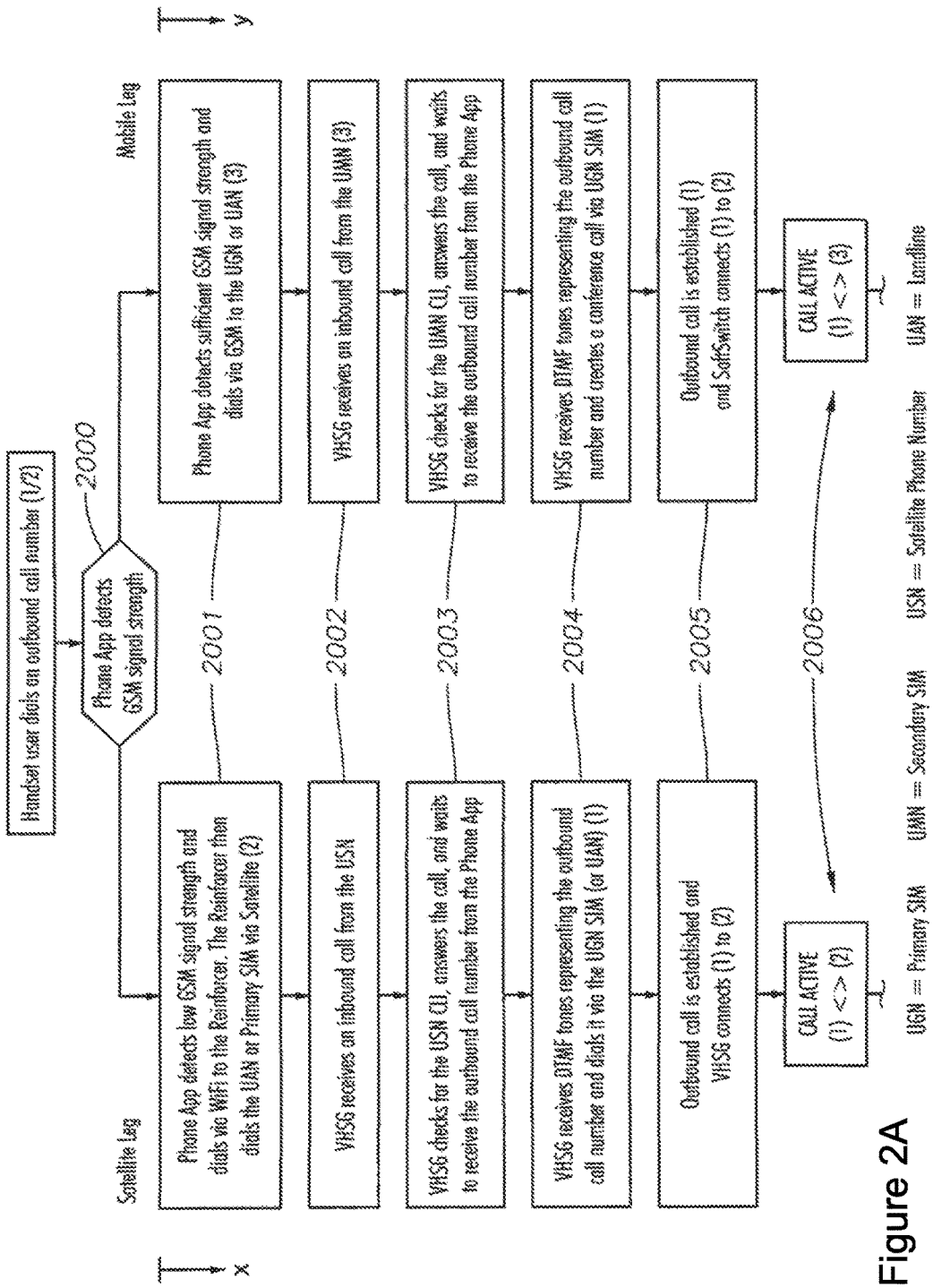
FIGS. 2A and 2B shows the flow of an outbound call from a mobile device in one embodiment of the system.
Figure 2B:
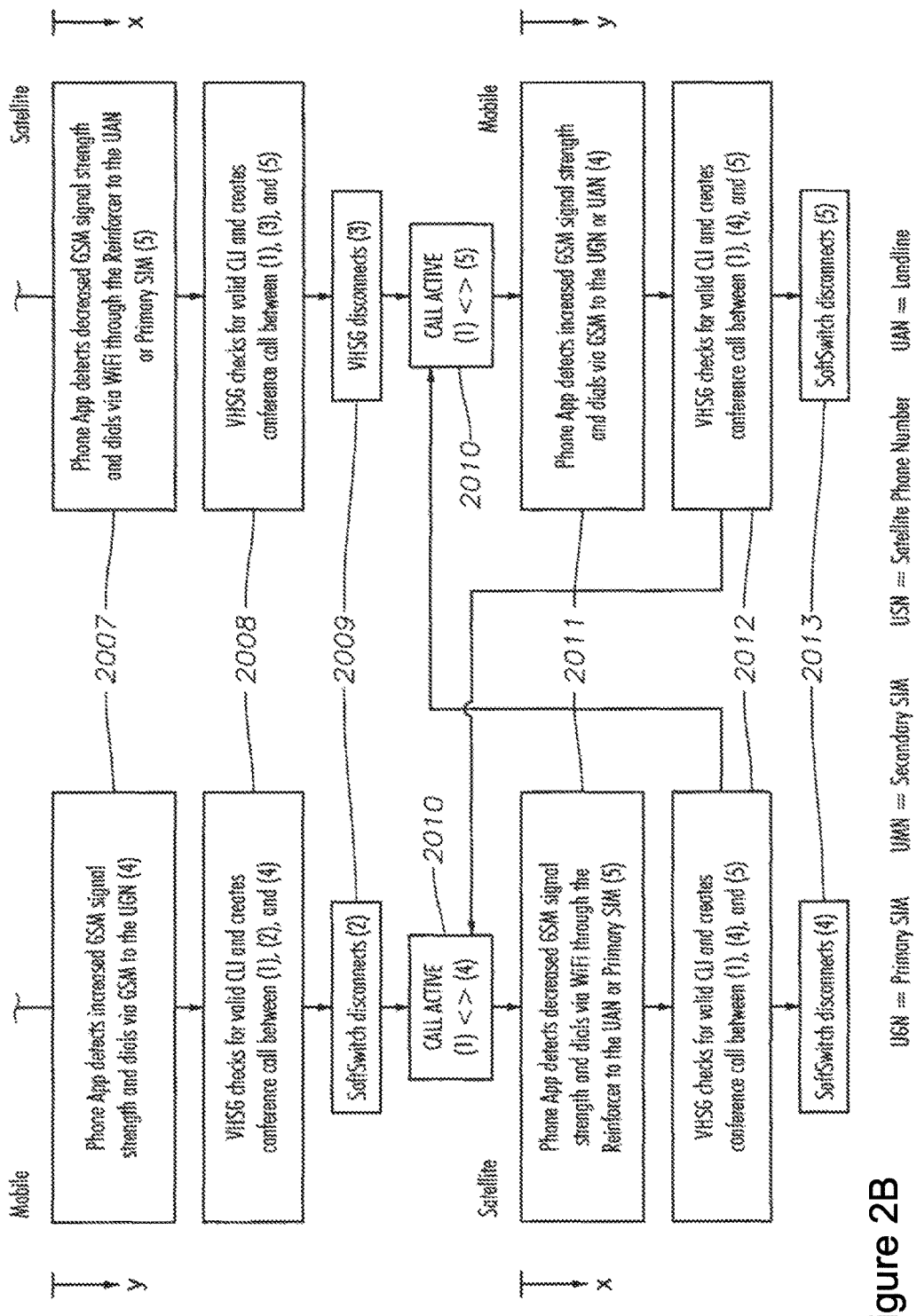

Outbound Calls (FIG. 1 and FIGS. 2A and 2B).

For outbound calls from the, mobile device 40, the mobile app will initially determine over which network to place the initial call (again, depending on mobile network strength, or possibly on user preference). The resident mobile application program on the mobile device 40 can store the number dialed by the subscriber (the called number), and the app will initiate an outbound call to the VHSG via the UAN or the primary SIM, (depending on the embodiment), over the network selected by the app (step 2001).

The VHSG recognizes an incoming call to the primary SIM card or UAN as originating from the secondary SIM or the USN (for instance, via caller ID) (step 2002). The VHSG recognizes this call as a new outbound call, as there is not a currently active call to the primary SIM card or UAN from the secondary SIM or USN (if a current call was in place, such a new incoming call would function as an indicator to transfer networks) (step 2002). The VHSG 90 "answers" this call (step 2002), and the mobile app is made aware of the pickup by the VHSG 90 via handshaking signals, and the VHSG 90 waits to receive the dialed number from the mobile device (step 2003). The mobile app recognizes that the call has been "answered" and subsequently transmits the called number to the VHSG 90 over the established call (such as sending IP packets, or frequency tones (e.g. DTMF tones)) (step 2004). The VHSG, upon receiving the dialed number via the secondary SIM, will initiate a conference call to the called number via the primary SIM or UAN (step 2004). If the dialed number was received, for instance, via the USN, the VHSG will initiate an outbound call via the primary SIM (step 2004X). Once the call is picked up by the dialed party, the VHSG bridges the call to the primary SIM card (or UAN) from the mobile device, with that to the dialed party placed by the VHSG (step 2005). The mobile application program may receive handshaking (for instance, forwarded by the reinforcer 100 as received through the active network, as appropriate) of the connection status in order for the mobile application program to make the call active on the mobile device 40. Alternatively, the call could be made active from the initial call, or after transmission of the designated number of the called party (not shown). In any event, at this point, a call is established with the called party, the mobile device (or mobile device via reinforcer) and the VHSG (step 2006). Transfer of a call between networks is handled similarly as in an incoming call, and is depicted in steps 2007-2010), and a second network switch depicted in steps 2011-2013.

The VHSG 90 processor anchors the call (remains on the conference call) and monitors the primary SIM (or UAN) for an incoming request to transfer to the passive network, as described above.

To facilitate communications over the various networks, the Softswitch will have suitable equipment and/or software, in communication with the processor, to allow communications via internet, mobile phone networks or PSTN, such as software to reformat incoming information into a form suitable to the outgoing transmission network (reformat, analog/digital converters, codecs schemes, a session initiated protocol server (SIP server) to format in IP packets, etc). This hardware/software is generally referred to as the reinforcer media changer, and the type of hardware and or software needed will depend on the particular satellite network, and the type of communication (e.g. voice, data, streaming media, packet switched, SMS, etc.).

The Reinforcer.

The reinforcer 100 is a hardware/software device that interfaces the satellite network and the mobile device, and includes a suitable antenna and radio transceiver, and may include a suitable satellite voice/data modem 34. Aspects of the reinforcer are shown in the block diagram of FIG. 5. An example, the signal reinforcer operatively communicates with a satellite network such as Globalstar's satellite network. To bi-directionally communicate with the satellite network of this example, the voice/data modem of the signal reinforcer may be a Globalstar voice/data modem (model 1720 or 1700).

The reinforcer 100 includes an additional interface that allows the reinforcer to communicate bi-directionally with the mobile device (generally, with the resident app on the mobile device designed to interface the reinforcer) via the air interface 35. The air interface 30 for wireless communication, can utilize WiFi communications, SIP communications, Bluetooth, or other local wireless communication with the mobile device. In some mobile devices, such as a tablet, the reinforcer interface may be a wired interface, such as provided by a USB port or Ethernet port connector, with the associated Ethernet or USB hardware needed for communications also located in the reinforcer. For WiFi communications, the interface can be a session initiation protocol (SIP) server 38. A SIP server is preferred to enable a SIP client (the mobile phone app) to use a standard high quality/high speed PCMU session with the reinforcer. Without the SIP server situated within the reinforcer, poor voice quality may be present as heavy compression could be required to fit a SIP stream into the non-transparent 7.2 k data async channel. The reinforcer 100, as a wireless communications device with the mobile device, provides functionality to the mobile device similar to that of a cellular phone tower. That is, the reinforcer creates an access point for wireless communication to the mobile device. The reinforcer, also contains the hardware/software to provide satellite communications, through the reinforcer, to the satellite network (not shown in FIG. 5).

By use of the reinforcer 100, the mobile device becomes an integrated mobile and satellite phone (note, for a prior integrated satellite/mobile phone, the reinforcer would not be needed, but an application would still be required on the mobile device to allow transfer between the mobile functionality and satellite functionality).

The reinforcer 100 also includes a processor (such as an ARM Core) 36 and associated memory which provides all of the needed routing tables and which assists in managing communications between the mobile device and satellite network. The processor 36 communicates with the interface 35. The reinforcer can include additional hardware and/or software to include integrated support for hosting one or more value added applications, such as SMS texting, email, internet web browsing, blue force tracking, or the like. The reinforcer 100 preferably includes a media changer 37 which is communicably connected to the satellite transceiver and or voice/data modem 34 and the processor 36. The reinforcer media changer 37 enables the reinforcer to format information for satellite transmission, or receipt from satellite transmission, for communication with the mobile device.

When the user is ready to make an outgoing call (or initiate an internet session, for instance), the mobile device resident application program gathers the necessary information input by the user (e.g. phone number if a voice call) and transmits this information to the reinforcer 100. The reinforcer 100 then generates the required information and issues serial commands to cause the satellite modem to connect to the satellite network to establish the communications path through the satellite network.

When the call is connected, the reinforcer 100 relays handshaking information to the resident app (or creates its own signals) to notify the resident app of the connection and for handling of the call with the user interface on the mobile device, and then to transfer data (such as voice data) input to the mobile device (e.g. microphone) and converted by the mobile to a digital data stream (or it may use the A/D converter output of the digital device, if present), to the reinforcer 40 for transmission over the satellite network (and also to send received data from the satellite network back to the mobile device). The reinforcer media changer, in conjunction with the processor 36, may need to convert the data streams from one format to another for transmission through the various devices (e.g. reinforcer interface to/from mobile, satellite data to/from interface, etc.) such as by using a modem, A/D converter, etc.

When the call is terminated, the handshaking information to take down the call is communicated through the reinforcer 100 to allow the mobile app to communicate such to the mobile device 40 for closing the call. Similarly, for an incoming call, the handshaking information is received and transmitted (or new handshaking signals created by the processor) by the reinforcer to the mobile resident app. The mobile app then internally communicates with the mobile device to establish an incoming call for the user to answer (e.g. provide a ring signal). When answered, handshaking is transmitted from the mobile device, through the reinforcer, back to the satellite network to establish the call.

The Resident App.

The mobile device also need a resident application program to provide the needed functionally to (1) communicate with the reinforcer; and (2) communicate with the mobile device. The resident app is thus the intermediary on the mobile device to handle communications between the mobile device and reinforcer, just as the reinforcer is the intermediary to handle communications between the resident app and the satellite network. As an example, when an outbound call is made from the mobile phone, the call is routed, via the WiFi link, to SIP Server on the reinforcer. Thereafter, the reinforcer's processor places an outbound call using the voice/data modem and routes the voice data via the media changer, using for instance, an analog interface. Conversely, when an inbound call is received by the voice/data modem, the reinforcer's processor receives the inbound call and initiates an outbound call to the SIP client of the mobile phone using its SIP server over the WiFi link.

As illustrated, the signal reinforcer 100 may be a stand-alone device that communicates with a mobile device, or alternatively, the reinforcer may be integrated into the hardware of the mobile device to provide satellite capability for an mobile device that lacks such capability to interface directly with a satellite communications satellite.

The signal reinforcer may include additional hardware or software features, such as security functionality to restrict non-authorized users from operating the device.

The invention claimed is:

1. A method of switching an active ongoing electronic communication at a mobile device from a first communications channel over a first network to a second communications channel over a second network, where said first network is one of a mobile cellular communications network or a satellite communications network and said second network is the other of said mobile cellular communications network or a satellite communications network, using a switch device located remotely from said mobile device, said switch device communicating with a second subscriber identity module (SIM) or re-usable identification module (RUIM) card, said second SIM or RUIM card located remote from said mobile device but being assigned to said mobile device and associated with said mobile device by said switch device, said mobile device comprising a cellular communications device and a satellite transceiver device physically separate from said cellular communications device but capable of communication with the cellular communications device over a short range wireless link, said satellite transceiver having a user satellite number assigned to the mobile device and said switch device is configured to communicate with a mobile cellular communications network and a satellite communications network; said method comprising the steps of:
   (1) said switch device receiving a notice communication, said notice communication directed to said second SIM card from said mobile device, where said mobile device cellular communications device includes a first SIM or RUIM card, said first SIM or RUIM card being assigned to said mobile device and associated with said second SIM or RUIM card by said switch device, said notice communication operating to indicate that a switch to said second network is desired;
   (2) said switch device initiating or establishing a second communications channel directed to said mobile device, where said second communications channel is configured to establish communications to said mobile device via said second network;
   (3) switching said ongoing electronic communication on said first communications channel on said first network to said second communications channel on said second network.

2. The method of claim 1 further including the step of termination of said electronic communication over said first network.

3. The method of claim 1 where said cellular communications device comprises a mobile smart phone.

4. The method of claim 1 where said switch device comprises a computer processor and an associated memory device.

5. The method of claim 3 where said switch device further comprises a softswitch, said softswitch further comprising a computer processor and associated memory devices.

6. The method of claim 1 wherein said first communication channel and said second communication channel are legs of a single conference call.

7. The method of claim 6 wherein said electronic communication is simultaneously ongoing on said first and second channels.

8. The method of claim 1 wherein said electronic communications to said mobile device over said satellite communications network are directed to said user satellite number.

9. The method of claim 1 wherein said step of switching said ongoing electronic communications from said first network to said second network includes the step of conferencing said ongoing communications over said first communications channel on said first network with said second communication channel over said second network.

10. A method of selecting, at a mobile device, a network over which to receive an incoming electronic communication, where said selection includes either a first network or a second network, where said first network is one of a mobile cellular communications network or a satellite communications network and said second network is the other of said mobile cellular communications network or a satellite communications network, said mobile device comprising a cellular communication device having a first subscriber identity module (SIM) or re-usable identification module (RUIM) card, said mobile device further comprising a satellite transceiver device physically separate from said cellular communications device but capable of communication with the cellular communications device over a short range wireless link, said satellite transceiver having a user satellite number assigned to the mobile device, the method comprising the steps of:
   (1) receiving at said mobile device a first notice communication, over said satellite communications network of a pending incoming electronic communication, said first notice communication received from a remotely located switch device, where said switch device is in communication with a second SIM or RUIM card that is located remote from said mobile device, said second SIM card being assigned to said mobile device and said first SIM or RUIM card associated with said second SIM or RUIM card by said switch device, and further associated with said mobile device by said switch device, where said switch device is configured to communicate with a mobile cellular communications network and a satellite communications network;
   (2) receiving a second notice communication at said mobile device over said mobile cellular communications network of a pending incoming electronic communication over said mobile cellular communications network, said second notice communication received from said remotely located switch device;
   (3) said mobile device determining if cellular signal strength is above or below a predetermined threshold limit;
   (4) if said cellular signal strength is above said threshold limit, said mobile device answering said incoming electronic communication over said mobile cellular communications network;
   (5) if said signal strength is below said threshold limit, said mobile device answering said incoming electronic communication over said satellite communications network.

11. A method of transferring or switching an ongoing electronic communication at a mobile device from a first communications channel over a first network to a second communications channel over a second network, where said first network is one of a mobile cellular communications network or a satellite communications network and said second network is the other of said mobile cellular communications network or a satellite communications network, and said mobile device comprises a mobile component having a first subscriber identity module (SIM) or re-usable identification module (RUIM) card and configured to operatively communicate over said mobile cellular communications network and a satellite component physically separate from said cellular communications component but capable of communication with the cellular component over a short range wireless link, configured to operatively communicate over said satellite communications network; said method comprising the steps of:

(1) determining at said mobile device the cellular signal strength of said mobile cellular communications network, and based on said cellular signal strength, determining to transfer from said first network to said second network;

(2) said mobile device sending a first notice communication directed to a second SIM or RUIM card where a switch device communicates with said second SIM or RUIM card and the second SIM or RUIM card being assigned to said mobile device, said second SIM or RUIM card located remote from said mobile device but said second SIM card being associated with said mobile device by said switch device, said first notice communication being sent over said second network or said first network, said first notice communication acting as a request to transfer from said first network to said second network;

(3) said mobile device receiving a second notice communication that a second communications channel for said ongoing communications is available on said second network;

(4) said mobile device transferring said ongoing communications from said first communications channel on said first network, to said second communications channel on said second network.

12. A system for switching electronic communications between a first network and a second network where said first network comprises one of a mobile cellular communications network or a satellite communications network and said second network comprises the other of said mobile cellular communications network or a satellite communications network; said system comprising a plurality of mobile devices, each comprising a satellite transceiver component for direct two way communications with a satellite in a satellite communications network and a cellular communications component for direct two way communications with a cell in a cellular communications network where said cellular communications component is physically separate from said satellite communications component but capable of communication with the satellite communications component over a short range wireless link; each of said mobile devices having a pair subscriber identity module (SIM) or re-usable identification module (RUIM) cards associated therewith; for each mobile device, one of said pair of SIM or RUIM cards assigned to said mobile device and located with said mobile device, the other of said pair of SIM or RUIM cards being assigned to said mobile device and located remote from said mobile device, and said pair of SIM or RUIM cards being associated with said mobile device in said switch device;

said switch device further being located remotely from said mobile devices; said switch device comprising a processor and a database, said switch device capable of establishing or initiating a first communication channel over said first network and a second communication channel over said second network to allow a communication, to a select one of said plurality of mobile devices, to be present simultaneously on said first communication channel and said second communications channel.

13. The system of claim 12 wherein for each of said plurality of mobile devices, said pair of associated SIM or RUIM cards are associated with said respective mobile device in said database of said switch device.

14. The system of claim 12 wherein said mobile device further comprises a session initiation protocol server.

15. The system of claim 12 wherein said cellular communications component further comprises a smart phone.

16. The system of claim 12 further comprising a simbank, said simbank storing a plurality of said SIM or RUIM cards, where for each of said mobile devices, one of said stored SIM or RUIM cards is one of said pair of SIM or RUIM cards that is associated with and located remotely from said mobile device.

17. The system of claim 12 where said short range wireless link is a WiFi link.

* * * * *